US011129568B2

(12) United States Patent
Olivier et al.

(10) Patent No.: US 11,129,568 B2
(45) Date of Patent: Sep. 28, 2021

(54) NON-INVASIVE PHYSIOLOGICAL QUANTIFICATION OF STRESS LEVELS

(71) Applicant: LifeQ Global Limited, Dublin (IE)

(72) Inventors: Laurence Richard Olivier, Alpharetta, GA (US); Franco Bauer du Preez, Cobham (GB); Shannagh Jane Hare, Cape Town (ZA); Alida Fanfoni, Stellenbosch (ZA)

(73) Assignee: LifeQ Global Limited, Dublin (IE)

( * ) Notice: Subject to any disclaimer, the term of this patent is extended or adjusted under 35 U.S.C. 154(b) by 359 days.

(21) Appl. No.: 15/330,865

(22) Filed: Nov. 7, 2016

(65) Prior Publication Data

US 2017/0181700 A1 Jun. 29, 2017

Related U.S. Application Data

(60) Provisional application No. 62/251,996, filed on Nov. 6, 2015.

(51) Int. Cl.
*A61B 5/00* (2006.01)
*A61B 5/16* (2006.01)
(Continued)

(52) U.S. Cl.
CPC ........ *A61B 5/4884* (2013.01); *A61B 5/02055* (2013.01); *A61B 5/14546* (2013.01);
(Continued)

(58) Field of Classification Search
CPC . A61B 5/4884; A61B 5/02055; A61B 5/0402; A61B 5/0476; A61B 5/14546;
(Continued)

(56) References Cited

U.S. PATENT DOCUMENTS

| 15,344,970 | 11/2016 | Olivier |
| 2004/0143170 A1* | 7/2004 | DuRousseau ............ A61B 5/16 600/300 |

(Continued)

FOREIGN PATENT DOCUMENTS

| WO | WO2014140960 | 9/2014 |
| WO | WO2015082231 | 6/2015 |

OTHER PUBLICATIONS

The International Search Report/Written Opinion issued by the U.S. Receiving Office for the corresponding international application, PCT/US2016/00105; 9 pages.
(Continued)

*Primary Examiner* — Lynsey C Eiseman
*Assistant Examiner* — Jessandra F Hough
(74) *Attorney, Agent, or Firm* — Smith, Gambrell & Russell LLP

(57) ABSTRACT

A data acquisition device includes measuring instruments to generate physiological and/or psychological data streams. Microprocessors within the acquisition device process the generated data streams into metrics, which feed into stress function algorithms. Algorithm processing may occur either on the device, or metrics may be communicated via wireless communication for external processing on mobile devices and/or cloud-based platforms. The calculated stress functions inform cloud-based computational systems biology-derived models describing the dynamics of hormones and neurotransmitters released in the body in response to stressful stimuli. Stress hormone levels are quantified using these models, and are used in combination to serve as biologically inspired metrics of acute and chronic stress an individual is experiencing.

17 Claims, 7 Drawing Sheets

(51) Int. Cl.
| | |
|---|---|
| *A61B 5/0205* | (2006.01) |
| *A61B 5/318* | (2021.01) |
| *A61B 5/369* | (2021.01) |
| *A61B 5/145* | (2006.01) |
| *A61B 5/11* | (2006.01) |
| *A61B 5/08* | (2006.01) |
| *A61B 5/053* | (2021.01) |
| *A61B 5/021* | (2006.01) |
| *A61B 5/024* | (2006.01) |
| *A61B 5/0533* | (2021.01) |

(52) U.S. Cl.
CPC .............. *A61B 5/165* (2013.01); *A61B 5/318* (2021.01); *A61B 5/369* (2021.01); *A61B 5/4041* (2013.01); *A61B 5/4227* (2013.01); *A61B 5/6814* (2013.01); *A61B 5/6823* (2013.01); *A61B 5/6824* (2013.01); *A61B 5/6826* (2013.01); *A61B 5/6828* (2013.01); *A61B 5/6831* (2013.01); *A61B 5/6833* (2013.01); *A61B 5/6861* (2013.01); *A61B 5/7264* (2013.01); *A61B 5/021* (2013.01); *A61B 5/02416* (2013.01); *A61B 5/053* (2013.01); *A61B 5/0533* (2013.01); *A61B 5/08* (2013.01); *A61B 5/0816* (2013.01); *A61B 5/11* (2013.01); *A61B 5/4035* (2013.01); *A61B 2560/0242* (2013.01); *A61B 2562/0219* (2013.01); *A61B 2562/0223* (2013.01)

(58) Field of Classification Search
CPC ..... A61B 5/165; A61B 5/4041; A61B 5/4227; A61B 5/6814; A61B 5/6823; A61B 5/6824; A61B 5/6826; A61B 5/6828; A61B 5/6831; A61B 5/6833; A61B 5/6861; A61B 5/7264; A61B 5/021; A61B 5/02416; A61B 5/053; A61B 5/0533; A61B 5/08; A61B 5/0816; A61B 5/11; A61B 5/4035; A61B 2560/0242; A61B 2562/0219; A61B 2562/0223; G06F 19/00

See application file for complete search history.

(56) References Cited

U.S. PATENT DOCUMENTS

| | | | |
|---|---|---|---|
| 2011/0061647 A1* | 3/2011 | Stahmann | A61B 5/0031 128/202.16 |
| 2011/0245633 A1 | 10/2011 | Goldberg | |
| 2012/0289790 A1 | 11/2012 | Jain et al. | |
| 2012/0290215 A1* | 11/2012 | Adler | G16H 50/30 702/19 |
| 2014/0121543 A1* | 5/2014 | Chan | A61B 5/0006 600/483 |
| 2014/0288401 A1* | 9/2014 | Ouwerkerk | A61B 5/0533 600/345 |
| 2015/0182129 A1* | 7/2015 | Colley | A61B 5/0205 600/301 |
| 2015/0238140 A1 | 8/2015 | La Belle et al. | |
| 2017/0319122 A1* | 11/2017 | Wild | G16H 10/20 |

OTHER PUBLICATIONS

Office Action with Restriction Requirement dated Mar. 22, 2019 issued for U.S. Appl. No. 15/344,970, filed Nov. 7, 2016; 5 pages.
The extended European search report issued in corresponding European application No. 16862598.6 by the European Patent Office dated May 21, 2019; 8 pages.

* cited by examiner

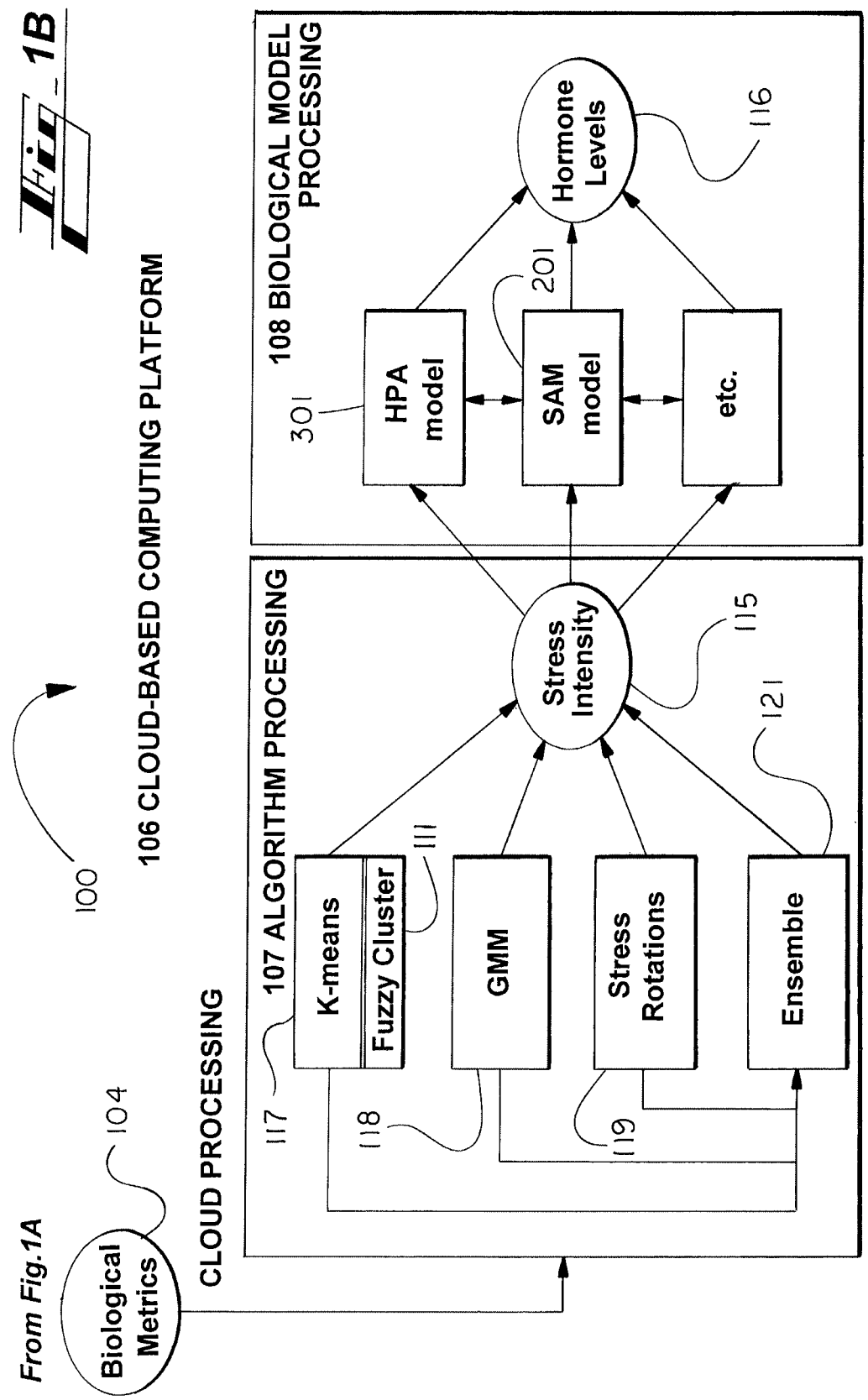

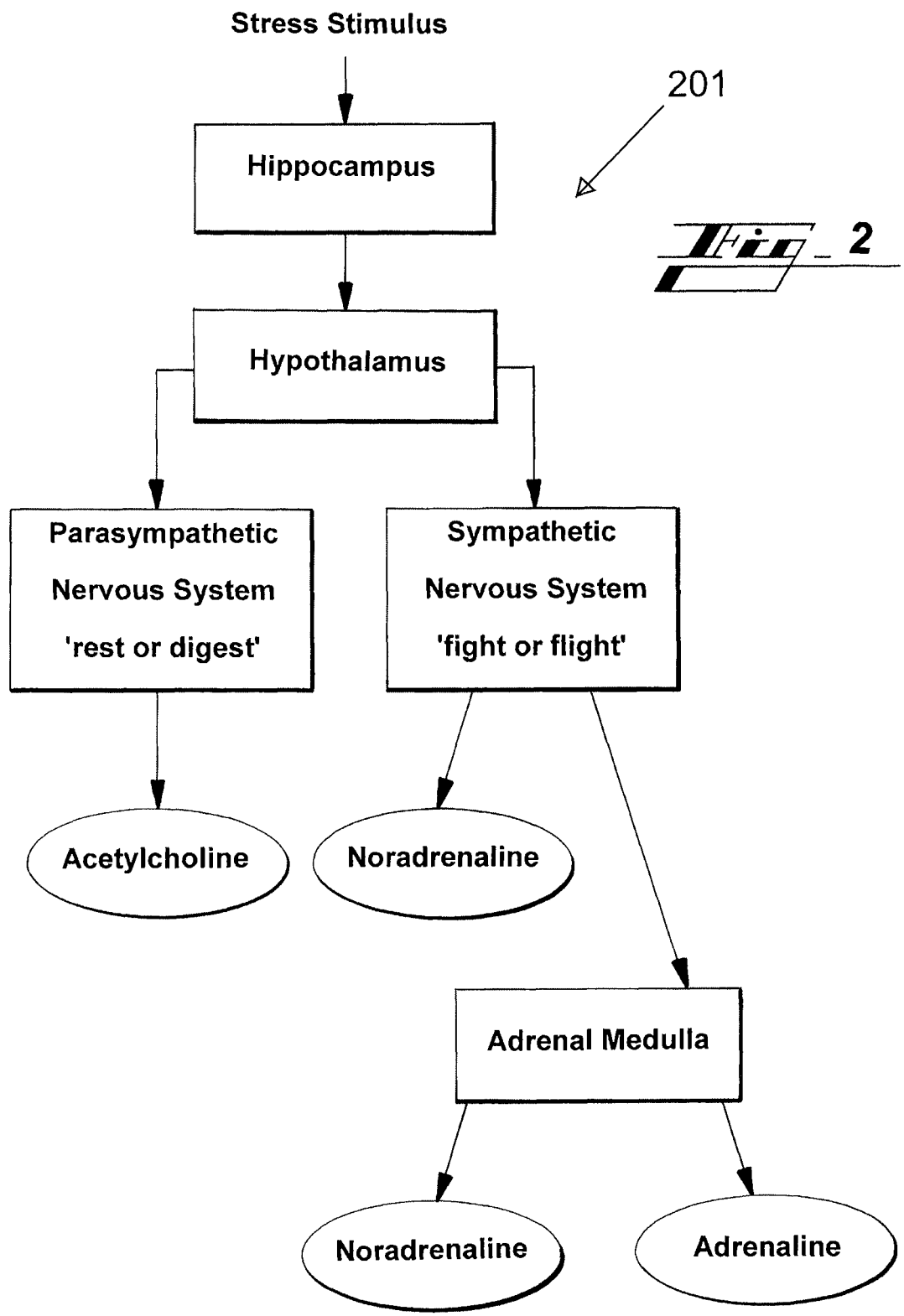

Test Subject-1

Test Subject-2

NON-INVASIVE PHYSIOLOGICAL QUANTIFICATION OF STRESS LEVELS

CROSS REFERENCE TO RELATED PATENT APPLICATIONS

This invention claims priority from U.S. Provisional Patent Application No. 62/251,996, filed Nov. 6, 2015, which is hereby incorporated by reference.

FIELD OF THE INVENTION

The present invention relates to the field of non-invasive digital health monitoring and signal processing. Specifically, the present invention relates to a system and method for non-invasive quantification of stress levels in a human subject.

BACKGROUND OF THE INVENTION

Stress is a fundamental problem in today's society. While young and healthy individuals may be able to handle bouts of acute stress, continual exposure to acute as well as chronic stress may have long-term effects that are harmful to health. A need exists to monitor stress levels to allow for better stress management and therefore a reduction in negative health effects related to stress.

Stress is a complex physiological and psychological phenomenon. Although a number of physiological and psychological stress measurements exist, no single gold standard metric for the quantification of acute and/or chronic stress exists. Existing stress measurements are considered too simplistic and/or invasive and/or hard to measure, and therefore, existing stress measurements do not offer reliable and/or continuous monitoring of stress levels. Challenges therefore remain to be able to quickly, continuously, accurately and non-invasively monitor an individual's stress levels in order to identify stressors, which will enable better management and improvement of overall stress levels and general well-being.

Definition of Stress

Biological or physiological stress is defined as the response of an organism to a stressor, such as an environmental condition or stimulus. Stress can be positive eustress), exemplified by, but not limited to, exercise, or negative (distress), exemplified by, but not limited to, work stress. With either stress, the body reacts accordingly to overcome each respective challenge or situation. Acute stress is defined as short-term stress driven by a specific situation, which can be interpreted as exciting and/or motivating (for example a rollercoaster ride) or scary (for example a near car accident). Stress can further be subdivided into psychological stress and physical or exercise stress. Chronic stress occurs when there is repeated exposure to a stressful situation, which leads to chronic activation of the stress response.

Control of Stress on a Biological Level

The stress response is controlled by the limbic areas of the brain such as the hippocampus, amygdala, and the hypothalamus, the portion in the brain that links the nervous system to the endocrine system via the pituitary gland. When an environmental sensory stimulus is perceived as a stressor by the limbic-prefrontal cortex of the brain, nerve impulses travel from the hippocampus and activate the posterior hypothalamus, which in turn trigger the sympathetic branch of the autonomous nervous system. This neural stress axis is the first to respond in reaction to a stressor, and it directly innervates target organs such as the heart to increase heart rate and cardiac output, as well as skeletal muscle activation. Noradrenaline is the main hormone released by the synaptic neurons that innervate these organs. The parasympathetic branch of the autonomous nervous system acts as counterbalance to rapid stress responses, and maintains homeostasis by the secretion of neural transmitters such as acetylcholine, which will lead to a decrease in heart rate and cardiac output.

In addition to direct innervation of target organs via the sympathetic nervous system, two main stress response pathways exist: the Sympathetic-Adreno-Medullary (SAM) axis and the Hypothalamus-Pituitary-Adrenal (HPA) axis. Activation of the SAM axis is a fast acting physiological response, and leads to an increased level of catecholamine hormones in the blood plasma and serum, including the "fight-or-flight" hormones adrenaline and noradrenaline. When a stressor has been processed by the limbic-prefrontal cortical interface of the brain, the hippocampus is stimulated, with subsequent stimulation of the hypothalamus followed by the adrenal medulla. Stimulation of the adrenal medulla results in a release of adrenaline and noradrenaline into the bloodstream, which activates the "fight-or-flight" response. Adrenaline is the primary hormone released at this stage, comprising 80% of the total secretion. This physiological response is rapid, and causes an increase in heart rate, blood pressure, cardiac output, sweating, and blood glucose levels. Crosstalk exists between the SAM axis and the HPA axis, because cortisol can also stimulate the medulla of the adrenal gland to produce adrenaline and noradrenaline. Once the stress has been dealt with, the parasympathetic nervous system is activated to inhibit the effect of the sympathetic nervous system, and homeostasis is restored.

Activation of the HPA axis is a relatively slow physiological response, and leads to an increased level of steroid hormones, including cortisol and aldosterone. Activation of the HPA axis starts with the release of corticotropin-releasing hormone (CRH) from the hypothalamus. CRH acts on the anterior lobe of the pituitary gland that releases adrenocorticotropic hormone (ACTH) upon CRH activation. ACTH travels through the bloodstream to stimulate the cortex of the adrenal gland, which subsequently results in the release of cortisol and aldosterone. Cortisol is a key regulator of the stress response and has widespread effects on the body, with its major roles including the promotion of glucose formation via gluconeogenesis and the redistribution of energy to critical organs such as the heart and brain, and furthermore suppresses unnecessary functions such as the immune response and reproduction. Cortisol levels peak ten to thirty minutes following a stressful event and levels can remain elevated for approximately an hour after the event. Aldosterone is another hormone secreted from the adrenal cortex, and is part of the reninangiotensin system, which regulates blood pressure by retaining sodium and water in the kidneys. While the body has negative feedback systems in place to ensure that the body returns to homeostasis after an acute stress stimulus, exposure to chronic stress causes this system to be over-stimulated, which may have severe health implications.

Other factors also affect the levels of cortisol, including age, gender, viral infections, sleep deprivation, caffeine consumption, and intense physical exercise. Cortisol levels are regulated in a circadian fashion, with cortisol levels subjected to a diurnal cycle. Cortisol levels are the highest in the early mornings, with levels decreasing throughout the day until it reaches its lowest levels at night, between three and five hours after the onset of sleep. The diurnal regulation of cortisol may change under abnormal physiological and psychological conditions, exemplified by, but not limited to, stress.

Current Methods of Stress Measurement

A number of psychological and physiological stress measurements exist, although no single gold standard metric for measuring stress exists. Heart rate variability (HRV) is the most commonly used measure of acute stress in academic literature as well as some commercial applications. Variability in heart rate occurs due to the opposing activities of the sympathetic and parasympathetic branches of the autonomous nervous system, which forms part of the SAM stress response pathway. However, it has been shown that HRV measurements are not a perfect representation of the sympathetic and parasympathetic systems and that these two systems are not correlated under all conditions. Research has shown that using HRV alone as a measurement of stress is an oversimplification of a complicated physiological process. Other measurements of stress that give an indication of SAM axis activation include heart rate, blood pressure monitoring, electrodermal activity measurement, respiratory rate measurement, and salivary a-amylase levels. Monitoring and quantification of stress levels is also achieved via assessment using psychological questionnaires. All of these measurements are considered too simplistic or invasive and/or hard to measure and therefore do not offer reliable and/or continuous monitoring of stress levels.

Research studies have shown that cortisol levels can be reliably sampled from saliva and peak ten to thirty minutes after the induction of stress. The hormone cortisol is a key regulator of the stress response, and is synthesized from cholesterol in the adrenal glands. Blood cortisol levels peak ten to thirty minutes following a stressful event. Levels remain elevated for approximately one hour after the event. Elevated levels of blood cortisol activate a negative feedback loop system, which leads to a reduction of cortisol production causing blood cortisol levels to return to baseline. This negative feedback mechanism ensures that the body returns to homeostasis following a stress stimulus. Blood cortisol levels therefore serve as a biological marker of stress. Salivary cortisol has therefore become one of the most popular biomarkers for stress studies, and is the gold standard metric for activation of the HPA axis. A caveat of salivary cortisol measurements is that salivary cortisol measurements do not perfectly compare with blood cortisol levels due to the fact that some salivary cortisol levels are due to cortisone activity in the mouth and that samples require laboratory analysis. Therefore, it is difficult to obtain quick results or to enable continuous monitoring.

U.S. Pat. No. 8,622,901 (Jain et. al.) describes a method for the continuous monitoring of stress in patients using accelerometer data combined with a number of other sensors including (but not limited to) heart-rate monitors, blood pressure monitors, pulse oximeters, and mood sensors. In order to enable continuous monitoring of stress levels using this method, a personalized stress profile is created for each individual patient from renal-Doppler sonography data, where the resistive index (R/I) of patients are used to calculate stress. A strong correlation exists between R/I and self-reported stress levels of patients. The relationship between R/I and self-reported stress levels are used to generate algorithms for calculating a stress index. The stress index is correlated with physiological and psychological data streams collected from the above-mentioned sensors, and a stress model for calculating the stress index as a function of physiological, psychological, behavioral, and environmental data is then determined. U.S. Patent Application Publication 2010/0022852 (Westerink et al.) describes a method for processing galvanic skin response (GSR) signals to estimate the level of arousal of a user. GSR sensors measure the electrical resistance of the skin. Arousal of the sympathetic branch of the autonomous nervous system leads to an increase in sweat gland activity, which leads to an increase in skin conductance. Skin conductance can therefore be a measure of stress responses. The particular embodiment describes a computer program product for processing GSR signals which when run, controls a computer to estimate a level of arousal. European Patent Application 2586365 (Sanchez Avila et. al.) describes a method for quantifying stress in a user, wherein the method allows for establishing discrimination between stressed users and relaxed users. The invention uses heart rate and GSR signals as data input, and utilizes stress patterns based on sigmoid transfer functions to allow quantifying stress in a larger number of situations. U.S. Patent Application Publication 2013/0281798 (Rau et al.) discloses methods for periodically monitoring the emotional state of a subject. Subjects are exposed to a plurality of stimuli during a session, wherein data is acquired through a plurality of physiological and psychological monitoring sensors. Data is transferred to a database, followed by data processing to extract objective information about the emotional state of a subject, specifically pertaining to emotional states including, but not limited to, anxiety disorder, depression, mood disorder, attention deficit hyperactivity disorder, autism spectrum disorder, and bipolar disorder.

There remains a considerable need for biologically inspired systems and methods that can accurately, quickly, continuously, and non-invasively quantify and monitor an individual's stress levels. As described herein, systems and methods for accurate, continuous and non-invasive quantification of biological stress levels are disclosed.

SUMMARY OF THE INVENTION

The present invention is a physiological and psychological quantification system that comprises a data acquisition device including measuring instruments to generate physiological and/or psychological data streams. A microprocessor within the data acquisition device processes the generated data streams into biological metrics that are fed into stress function algorithms. Algorithm processing may occur either on the data acquisition device, or the biological metrics may be communicated via a wireless communication link for external processing on mobile devices and/or a cloud-based computing platform. The cloud-based computing platform calculates stress intensity and uses the calculated stress intensity and biology-derived models to describe the dynamics of hormones and neurotransmitters released in the body in response to stressful stimuli. Stress hormone levels are quantified using the biology-derived models, and are used in combination to serve as biologically inspired metrics of acute and chronic stress an individual is experiencing.

For example, the data acquisition device is attached to the body of a human subject by, but not limited to, a wrist band, chest strap, chest patch, head band, upper arm band, upper arm patch, implant, ingestible, or nanotechnology. The measuring instruments capture signals exemplified by, but not limited to, physiological and psychological signals. External or predetermined data or data streams exemplified by, but not limited to, Doppler sonography data, psychological assessment data, and captured patient data during monitoring sessions are not required. The data streams generated by the measuring instruments are processed by a microprocessor, contained within the data acquisition device, into digital measurements that are further processed into biological metrics. The biological metrics are fed to stress function algorithms that provide a coarse level prediction of eustress and/or distress levels, and predictions may be given as stress intensities (0-100%). The biological metrics may also be obtained from databases to feed into the stress function algorithms. The stress function algorithm processing occurs on the data acquisition device, or the biological metrics are sent via a wireless communications link to a mobile device with an internet connection, or to a cloud-based computing platform, for stress function algorithm processing. Coarse level stress predictions inform biomathematical stress models that describe the dynamics of hormones and neurotransmitters released in the body upon stress. Specific stress hormone levels are estimated from these biomathematical stress models via stress function algorithm processing, and the calculated stress hormone levels may serve as readout for the human subject. The stress hormone and neurotransmitter estimations may be used in combination to compute biologically inspired quantifiable metrics of acute and chronic stress. The quantified stress metrics are relayed back from the cloud-based computing platform through the wireless communications link to the mobile devices and/or to the data acquisition device for display and/or notification to the user of his or her biological stress levels. The quantified stress metrics and/or the modeled stress hormone and neurotransmitter estimations can also be relayed to third party databases and/or mobile devices via an internet communications link. Examples of third parties include, but are not limited to, clinical, insurance, and retail parties. A condensed version of cloud-based biomathematical stress models can also be sent to the data acquisition device to enable stress hormone and neurotransmitter estimations and calculations of the quantifiable stress metrics on the data acquisition device itself.

Further objects, features and advantages will become apparent upon consideration of the following detailed description of the invention when taken in conjunction with the drawings and the appended claims.

BRIEF DESCRIPTION OF THE DRAWINGS

FIGS. 1A and 1B together are a schematic representation illustrating the stress quantification system in accordance with the present invention.

FIG. 2 is a schematic representation of the SAM stress axis, illustrating the biological control processes modeled by ordinary differential equations on a cloud-based computing platform in accordance with the present invention.

DETAILED DESCRIPTION OF THE PREFERRED EMBODIMENTS

Glossary of Acronyms

| | |
|---|---|
| ACC | Accelerometer |
| ACTH | Adrenocorticotropic Hormone |
| API | Application Program Interface |
| BP | Blood Pressure |
| BR | Breathing Rate |
| CRH | Corticotropin Releasing Hormone |
| CSB | Computational Systems Biology |
| DSP | Digital Signal Processing |
| ECG | Electrocardiogram |
| EDA | Electrodermal Activity |
| EEG | Electroencephalogram |
| GMM | Gaussian mixture model |
| GSR | Galvanic Skin Response |
| GYRO | Gyroscope |
| HPA | Hypothalamus - Pituitary-Adrenal |
| HRV | Heart rate variability |
| MAG | Magnetometer |
| PPG | Photoplethysmography |
| SAM | Sympathetic-Adreno-Medullary |
| TRAIT | State-Trait Anxiety Inventory |
| TSST | Trier Social Stress Test |

Figure 1A:
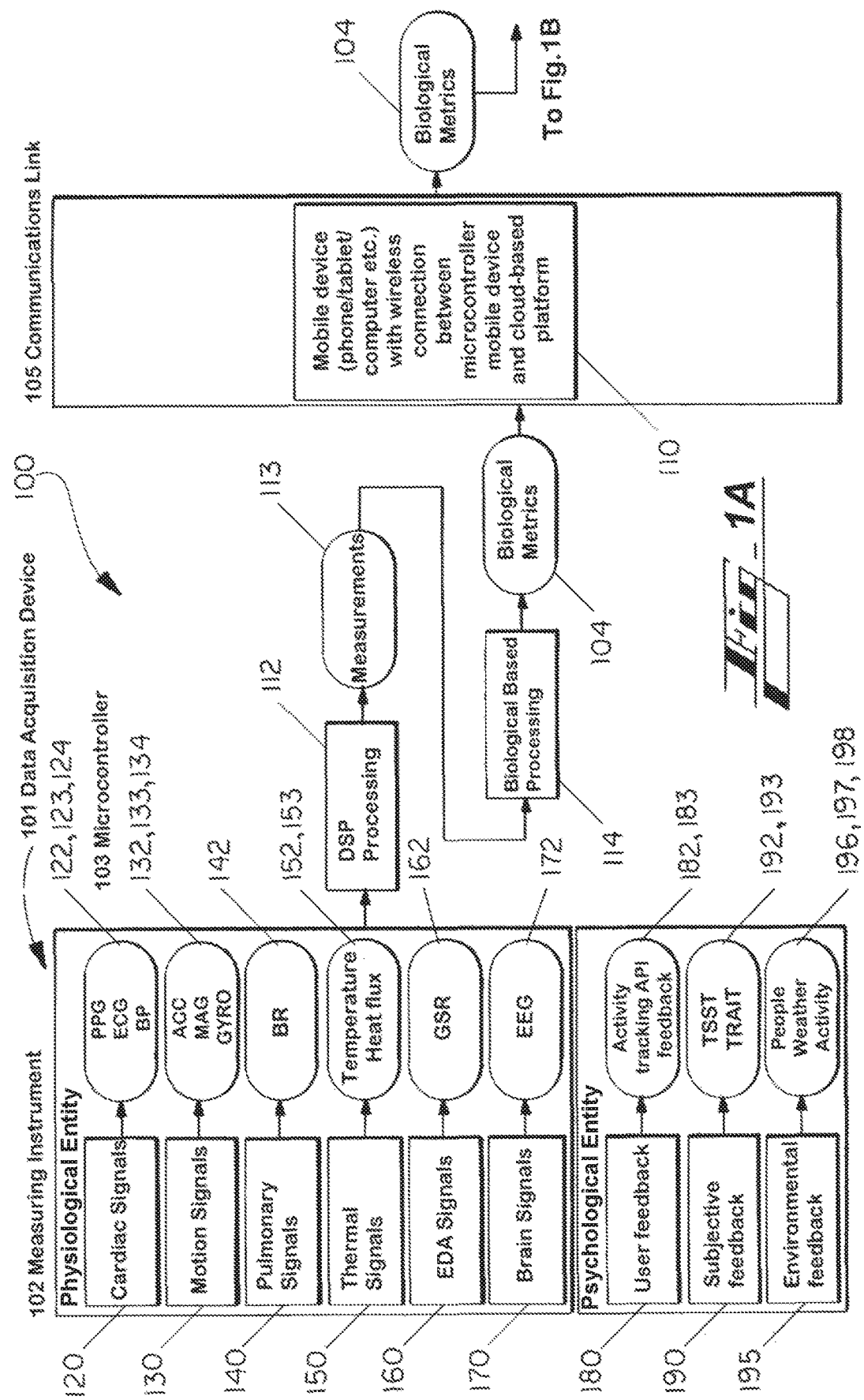

With reference to FIGS. 1A and 1B, a physiological and psychological stress quantification system 100 measures and predicts stress for a human subject. The physiological and psychological stress quantification system 100 comprises a data acquisition device 101 that is connected to the body of a human subject by, for example, but not limited to, a wrist band, chest strap, chest patch, head band, upper arm band, upper arm patch or via implant, ingestible, or nanotechnology. The data acquisition device 101 comprises measuring instruments 102, capable of capturing signals exemplified by, but not limited to, physiological and psychological signals. Physiological signals may include, but are not limited to, cardiac, motion, audio, pulmonary, thermal, electrodermal, and brain signals. Psychological signals may include, but is not limited to, user feedback, subjective feedback, and environmental feedback. With reference to FIG. 1A, the measuring instrument 102 captures physiological data including cardiac signals 120 (such as photoplethysmography PPG 122, electrocardiogram ECG 123, and blood pressure BP 124), motion signals 130 (such as accelerometer ACC 132, magnetometer MAG 133, and gyroscope GYRO 134), pulmonary signals 140 (such as breathing rate BR 142), thermal signals 150 (such as temperature 152 and heat flux 153), EDA signals 160 (such as galvanic skin response GSR 162), and brain signals 170 (such as electroencephalogram EEG 172).

With further reference to FIG. 1A the measuring instruments 102 also capture psychological data including user feedback 180 (activity tracking 182 and API feedback 183), subjective feedback 190 (TSST 192 and TRAIT 193), and environment feedback 195 (people 196, weather 197, and activity 198).

Data streams obtained from the measuring instrument 102 are converted to digital signals by digital signal processing DSP module 112 of microcontroller 103, or by processing within the measuring instruments 102, to give measurements 113. The measurements 113 are subjected to biological based processing by biological based processing module 114 of the microcontroller 103 to generate biological metrics 104 from the microcontroller 103. Additional data streams for biological based processing may also be obtained from databases, for example, but not limited to, medical and genetic databases. In particular embodiments, the biological metrics 104 are processed by the microcontroller 103 within the data acquisition device 101. In other embodiments, the biological metrics 104 are sent via a wireless communication link 105 to a mobile device 110 exemplified by, but not limited to, a smartphone, tablet computer, or laptop computer, with an internet connection for communication to a cloud-based computing platform 106.

The biological metrics 104 serve as input for stress function algorithm module 107 on the cloud-based computing platform 106. In other embodiments, the biological metrics 104 may also serve as input for stress function algorithm processing on the data acquisition device 101. In particular embodiments, using the biological metrics 104 as input for stress algorithm processing (module 107), either on the data acquisition device 101 or on the cloud-based computing platform 106, a generalized model is described that predicts whether a subject is in a state of acute mental stress or not. In other embodiments, a model is described that can quantify the level of stress a subject is experiencing given the data and the biological metrics 104 acquired from the data acquisition device 101 using statistical methods embodied in stress function algorithm module 107 to provide a coarse level prediction of stress intensity (0-100%). In preferred embodiments, data acquired from the coarse level prediction is used in the biomathematical model module 108 that quantifies the level of acute and chronic stress that a subject is experiencing physiologically, by estimating stress hormone and neurotransmitter levels, including, but not limited to, adrenaline, noradrenaline, acetylcholine, CRH, ACTH, cortisol, and aldosterone.

In particular embodiments, stress hormone and neurotransmitter estimations are used in combination to serve as biologically inspired quantifiable metrics of acute and chronic stress. The quantified stress metrics, such as stress intensity 115, are relayed back to the data acquisition device 101 from the cloud-based computing platform 106 through the wireless communication link 105 to the mobile devices 110 (part of the communication link 105) and/or to the data acquisition device 101 for display and/or notification to the user of his or her biological acute and/or chronic stress levels. In particular embodiments the quantified stress metrics, such as stress intensity 115 and/or modeled stress hormone and neurotransmitter estimations 116 can also be relayed to third party databases and/or mobile devices via internet communications. Examples of third parties include, but are not limited to, clinical, insurance, and retail parties. A condensed version of cloud-based biomathematically-derived stress models 108 can also be sent to the data acquisition device 101 or the mobile device 110 to enable the stress hormone and neurotransmitter estimations 116 and calculations of quantifiable stress metrics on the data acquisition device 101. Condensed or simplified personal stress models can also be transmitted to the data acquisition device 101 or the mobile device 110.

Stress Function Algorithms the biological metrics 104 from microcontroller 103 contained within the data acquisition device 101 are sent via the wireless communications link 105 to the mobile device 110 with an internet connection for communication to the cloud-based computing platform 106 for processing by stress function algorithm module 107. In other embodiments, stress function algorithm processing (module 107) of the biological metrics 104 occurs on the data acquisition device 101. In particular embodiments, the stress function algorithms in the stress function algorithm module 107 analyze the biological metrics 104 derived from the microcontroller 103. Particularly, the biological metrics 104 are analyzed by cluster analysis. Cluster analysis is the act of grouping a set of objects in such a way that objects in the same group (called a cluster) are more similar to each other than to those in other clusters. An example of cluster analysis is k-means clustering 117, which is used to classify measurements, the biological metrics 104, derived from the data acquisition device 101 into different stress and activity level states. Another example of cluster analysis is fuzzy clustering implemented by fuzzy clustering analysis module 111. Fuzzy logic is a form of computer logic, the output of which is a continuum of values between 0 and 1 which can also be represented as 0-100%. The system starts by assigning a set of membership functions for each input and a set for each output. A set of rules for the membership function is then applied. In particular embodiments, the algorithm allows the k-means clusters (module 117) to inform the shape of the membership function. Fuzzy clustering (module 111) provides an indication of the percentage of which of the features in the data belong to a particular cluster or state. It is therefore possible to determine the level of stress (from 0-100%) that a subject is experiencing. The output of fuzzy clustering is a stress function that fluctuates with time as stress levels rise and fall. A Gaussian mixture model (GAM) module 118 is another example of clustering model. The GMM model assumes that all the data points are generated from a finite number of Gaussian distributions with unknown parameters. In particular embodiments, the GMM model offers an advantage by combining the clustering process and the stress function calculation in one model. In particular embodiments, a stress rotation model module 119 is used for the classification of acute and chronic stress and exercise events. Vector directionality of data points on a parametric plot may be visualized as loops or "rotations". Rotational measurements may correspond to stress or exercise events. In order to capture and quantify the information generated by rotations, an algorithm calculates the area of rotations for both stress and exercise. The area is output as a stress function indicating the duration and severity of the stress or exercise event. This model offers an advantage over clustering techniques in that it has the ability to predict both acute mental stress and exercise at the same time. In other embodiments, stress intensities are calculated by using a combination of K-means clustering, fuzzy clustering GMM, and stress rotation algorithms. The above-mentioned theory and methods are used to create an ensemble 121 to classify stress events. Stress intensities are subsequently calculated using, as an example, but not limited to, logistic regression functions using a minimum of one biological metric as input to guide the intensity.

SAM Axis Model (FIG. 2)

In particular embodiments, stress functions, as determined from the above-described algorithms (module 107, FIG. 1B), inform ordinary differential equation (ODE)-based models of the SAM stress pathway 201 illustrated in FIG. 2. These computational system biology derived-models (module 108, FIG. 1B) describe the dynamics of hormones and neurotransmitters that are released in response to a stressful stimulus and therefore provide insight into the likely levels of hormones, including, but not limited to, adrenaline, noradrenaline, and acetylcholine, circulating in an individual's bloodstream. Parameter inputs that are found in the literature, such as binding efficiencies of hormone receptors and half-lives of hormones, together with the outputs from the combination of stress function algorithms (module 107) as described above, are used as the major input for ODE models describing the SAM axis. In particular embodiments, this model provides an estimation of adrenaline and noradrenaline levels in the body.

Figure 3:
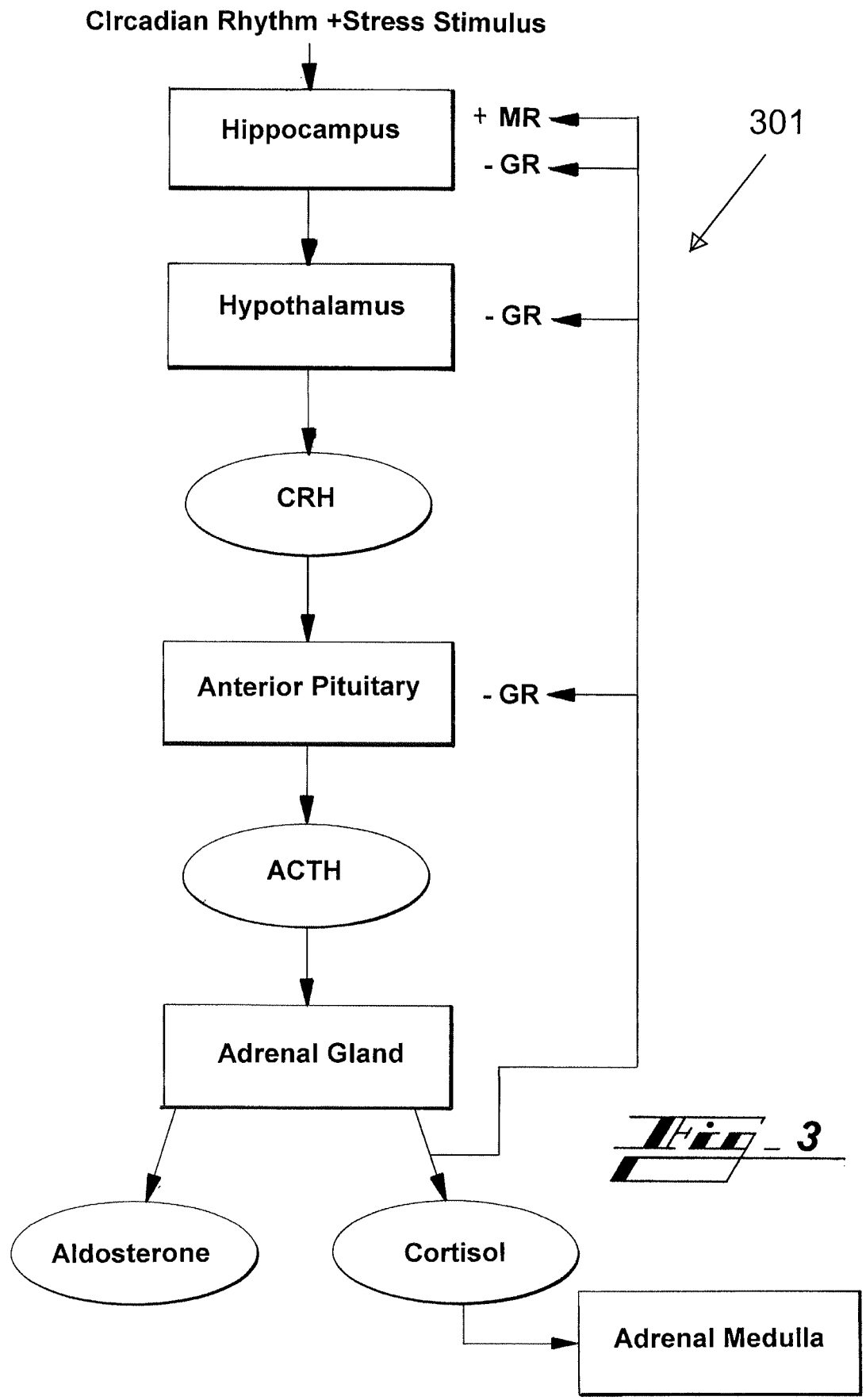
FIG. 3 is a schematic representation of the HPA stress axis, illustrating the biological control processes modeled by ordinary differential equations on a cloud-based computing platform in accordance with the present invention.

HPA Axis Model (FIG. 3)

In particular embodiments, stress functions, as determined from the above-described stress function algorithms (module 107), inform ordinary differential equation (ODE)-based models of the HPA stress pathway 301 illustrated in FIG. 3. These computational system biology derived-models (module 108) describe the dynamics of hormones and neurotransmitters that are released in response to a stressful stimulus (circadian rhythm+stress stimulus) and therefore provide insight into the likely levels of hormones, including, but not limited to, corticotropin-releasing hormone (CM), adrenocorticotropic hormone (ACTH), cortisol, and aldosterone circulating in an individual's bloodstream. Parameter inputs that are found in the literature, such as binding efficiencies of hormone receptors and half-lives of hormones, together with the outputs from the combination of stress function algorithms as described above, are used as the major input for ODE models describing the HPA axis model. In particular embodiments, this model provides an estimation of CRH, ACTH, cortisol, and aldosterone levels in the body.

Figure 4:
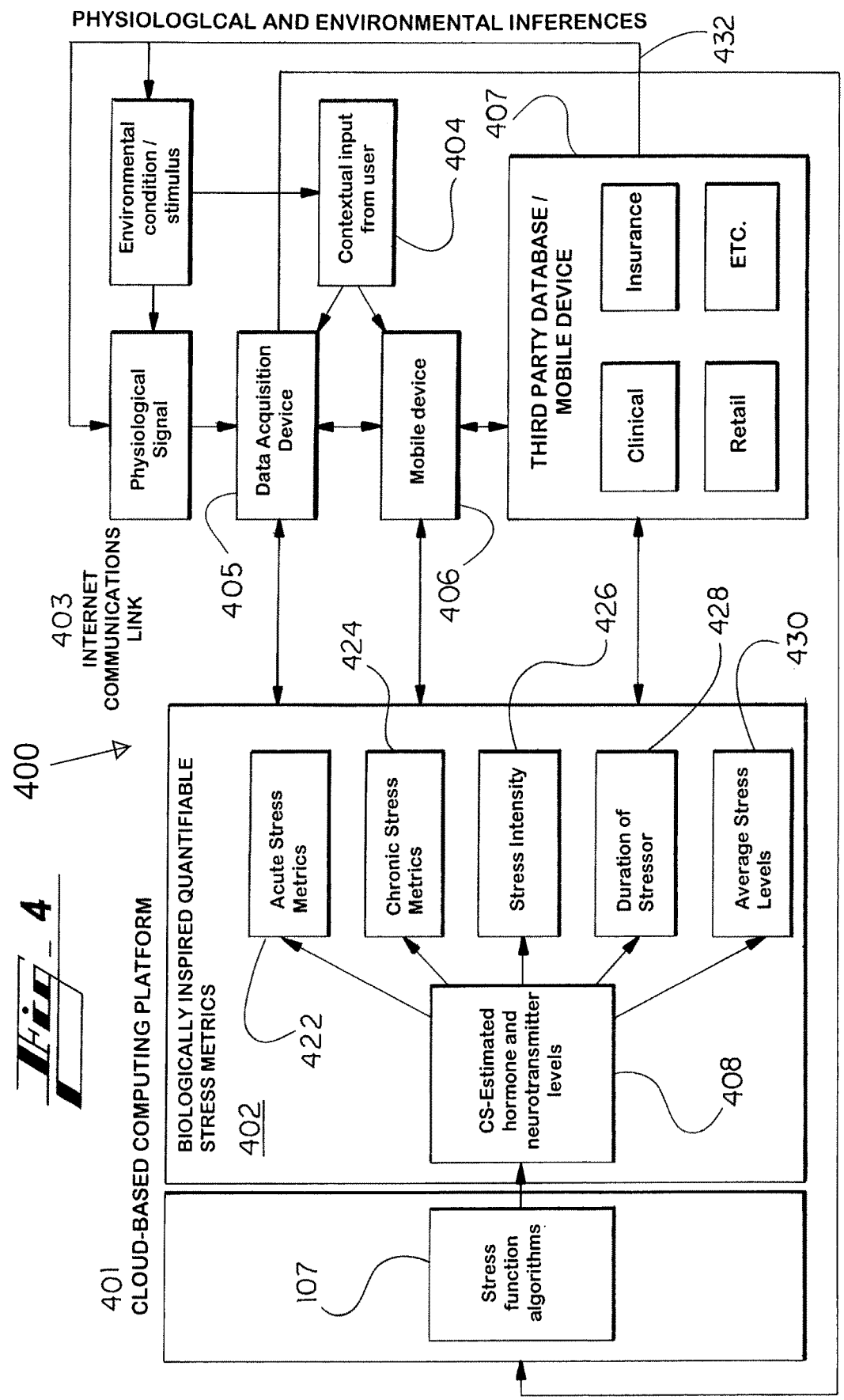
FIG. 4 is a schematic representation of a non-invasive stress quantification system in accordance with the present invention.

Biologically Inspired Quantifiable Metrics of Acute and Chronic Stress (FIG. 4)

With reference to FIG. 4, the cloud-based biomathematical models (108, 201, 301, 402) use estimated stress hormone and neurotransmitter levels as inputs to calculate combinatory stress metrics exemplified by, but not limited to, the amount of chronic and acute stress an individual is experiencing, duration of the stressor, stress intensities, and average stress levels. In other embodiments, condensed versions of cloud-based biomathematical models are sent to a data acquisition device 405 or a mobile device 406, to enable stress hormone and neurotransmitter estimations and calculations, as well as display, quantifiable stress metrics 402 on the data acquisition device 405. Input for biomathematical models includes, but is not limited to, the HPA axis input 301, the SAM axis input 201, and sympathetic and parasympathetic nerve axis input. In particular embodiments, the quantified metrics 402 are sent from the cloud-based computing platform 401 to the data acquisition device 405 or the mobile device 406 as readout via a wireless communications link 403. In other embodiments, the quantified metrics 402 may be relayed from the cloud-based platform 401 through the wireless communication link 403 to the mobile device 406 for display and/or notification to the user of his or her biological stress levels. Hormone and neurotransmitter estimations 408 include, for example, acute stress metrics 422, chronic stress metrics 424, stress intensity 426, duration of stressor 428, and average stress levels 430. The hormone and neurotransmitter estimations 408 can also be relayed from the cloud-based computing platform 401 and/or the mobile device 406 to third party databases and/or third-party mobile devices 407 via internet communications link 403. Examples of third parties 407 include, but are not limited to, clinical, insurance, and retail parties. Contextual information may be inferred from the quantified stress metrics 402 by third parties 407, to gain insight into physiological and environmental conditions/stimuli pertaining to the patient/client.

Figure 5A:
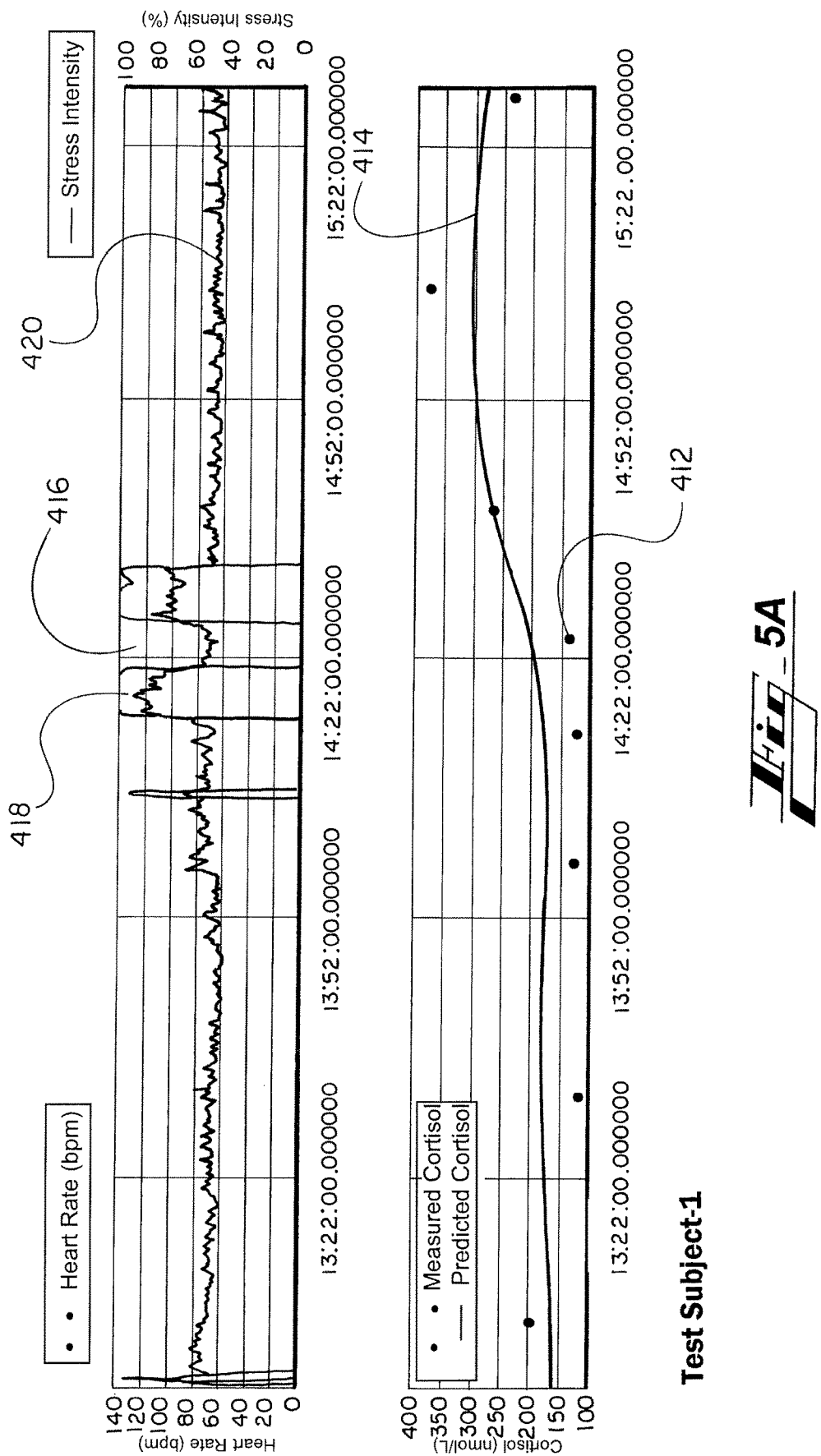
FIGS. 5A and 5B are charts that illustrate a comparison of measured salivary cortisol levels and model-predicted cortisol levels of two different test subjects obtained during a Trier Social Stress Test (TSST).
Figure 5B:
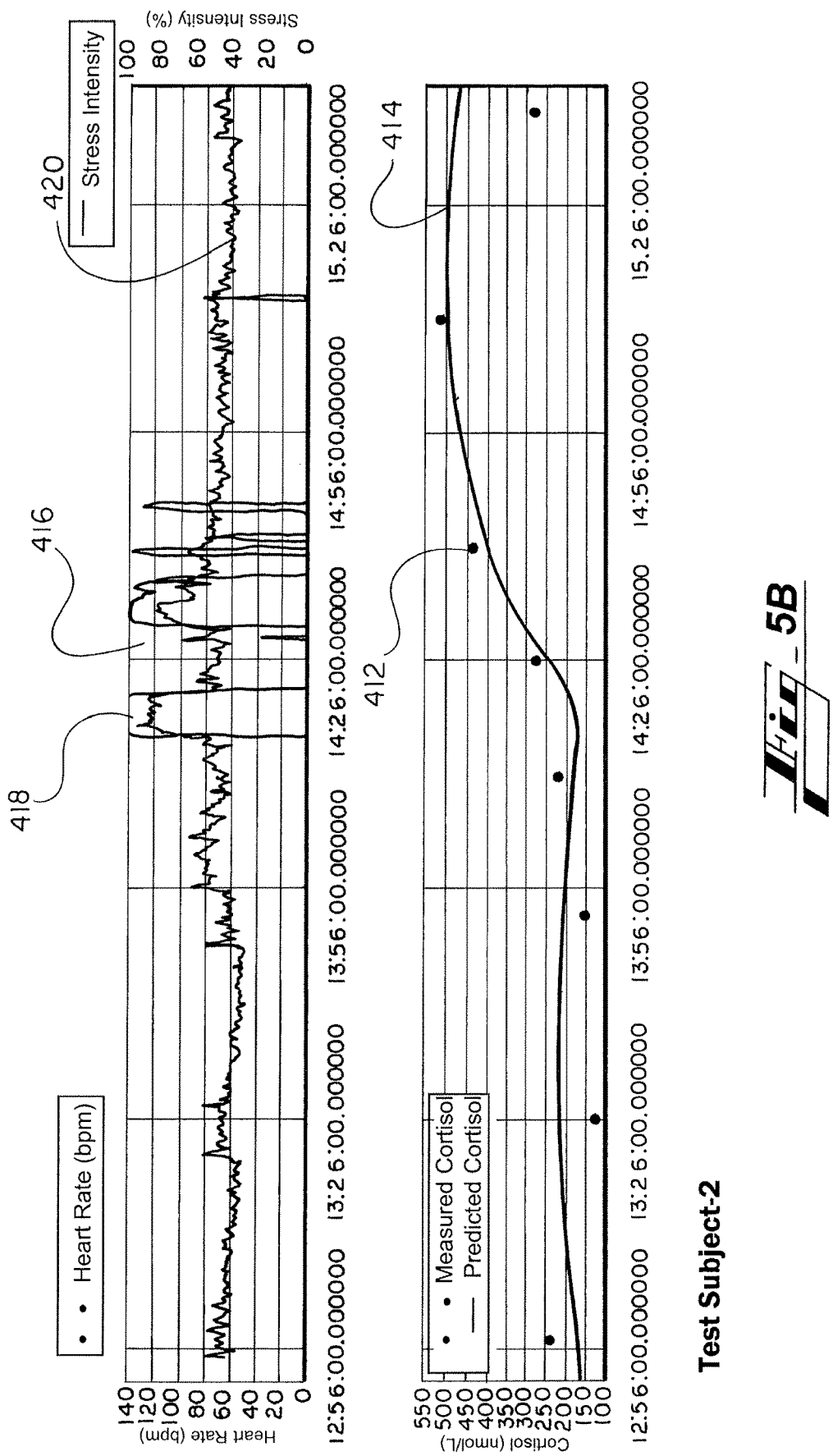

FIG. 5 shows examples of comparisons of measured salivary cortisol levels and HPA model-predicted cortisol levels of two different test subjects obtained during a Trier Social Stress Test (TSST).

USER EXAMPLE 1

In one embodiment of the invention, the data acquisition device 405 gathers physiological signals from a human subject wearing the data acquisition device 405. The subject provides context for stress events 404 (FIG. 4) via brief interactions with the interface of the data acquisition device 405 or the mobile device 406. Examples of the context include persons with whom the patient interacted, meetings, social settings, or any other information that might have relevance to the occurrence of the stress state. The subject receives daily, weekly, and monthly statistics on his or her stress levels. Examples of stress levels may include, but are not limited to, the average level of stress and the intensity as well as duration of the stressor, and the quantifiable stress metrics 402. The more context the user provides, the more relevant the information provided to the user can be. The clinical third parties 407 may access the contextual data on a third party database and/or mobile device 406 to make physiological and environmental inferences 432 (FIG. 4) to aid in prescribing relevant medication, improve current prescribed medications, diagnose new, and/or unknown stressors, and gain additional insight into the user's overall lifestyle and health for improved prognoses. FIG. 5 shows a comparison of measured salivary cortisol levels 412 and model-predicted cortisol levels 414 of two different test subjects obtained during a Trier Social Stress Test (TSST). The areas 416 in FIG. 5 indicate where stress is detected, using stress rotation algorithms. The areas 418 indicate high stress intensities experienced. The line 420 indicates heart rate, the solid dots 412 show measured cortisol levels, and the line 414 representing predicted cortisol levels 414 with the HPA axis model.

USER EXAMPLE 2

In one embodiment of the invention, the data acquisition device 405 gathers physiological signals on a psychiatry or psychology patient and infers periods of likely biological stress. In lieu of the data acquisition device 405 and the physiological quantification system 400, such a stressful experience would typically be analyzed as part of a psychiatry/psychology session where the patient recalls the context surrounding the event weeks after the fact (if at all) to aid the clinician towards an optimal treatment program. With the physiological stress quantification system 400 of the present invention, the stress state could be validated or questioned by the user and the context surrounding it can be gathered later the same day under less stressful circumstances as identified by the data acquisition device 405 (FIG. 4), using a brief interaction with the mobile device 406 in contact with the data acquisition device 405 or directly through the interface of the data acquisition device 405. This has the dual advantage of capturing the occurrence and context 404 surrounding stressful events in a way that is not possible in lieu of the invention. Examples of the context include persons with whom the patient interacted, meetings, social settings, or any other information that might have relevance to the occurrence of the stress state.

While this invention has been described with reference to preferred embodiments thereof, it is to be understood that variations and modifications can be affected within the spirit and scope of the invention as described herein and as described in the appended claims.

What is claimed:

1. A system for physiological and psychological quantification of stress levels of a human subject comprising the following:
   a. a data acquisition device including:
      i. a measuring instrument for acquiring physiological data and psychological data from the human subject, the physiological data is cardiac signals, motion signals, pulmonary signals, thermal signals, electrodermal activity signals, or brain signals and the psychological data is user feedback, subjective feedback, or environmental feedback;
      ii. a microcontroller for processing of the acquired physiological data and psychological data into biological metrics;
   b. a communication link; and
   c. a computing platform connected to the communication link for:
      i. receiving the biological metrics from the data acquisition device; and
      ii. processing the biological metrics into quantifiable stress metrics by means of a stress function algorithm module to calculate an estimate of levels of hormones or neurotransmitters released by the human subject and therefore the level of stress experienced by the human subject.

2. The system of claim 1, wherein the measuring-instrument is an implant device, an ingestible device, a nanotechnology device, a chest strap, a chest patch, a head band, an upper arm band, an upper arm patch, a wrist band, a finger band, a finger patch, an arm sleeve, or a leg sleeve.

3. The system of claim 1, wherein the algorithm module is a K-means clustering analysis module, a fuzzy clustering module, a Gaussian mixture model module, a stress rotation model module, and an ensemble of the K-means cluster analysis module, the fuzzy clustering module, the Gaussian mixture model module, or the stress rotation model module.

4. The system of claim 1, wherein the computing platform uses the biological metrics to estimate hormones and/or neurotransmitters released by the human subject during activation of a SAM stress axis.

5. The system of claim 1, wherein the computing platform uses the biological metrics to estimate hormones and/or neurotransmitters released by the human subject during activation of the HPA stress axis.

6. The system of claim 1, wherein the stress level experienced by the human subject is average stress levels, levels of acute stress, levels of chronic stress, stress intensity, duration of stressor, levels of distress, or levels of eustress.

7. The system of claim 1, wherein the computing platform is a cloud-based computing platform that receives the biological metrics from the microcontroller of the acquisition device by means of the communication link.

8. The system of claim 1, wherein the system includes a third-party database and the quantified stress metrics are sent to the third-party database by means of the communication link.

9. The system of claim 1, the computing platform for determining the quantifiable stress metrics from the biological metrics resides on a mobile device connected to the data acquisition device by the communication link.

10. The system of claim 1, the computing platform for determining the quantifiable stress metrics from the biological metrics resides on the data acquisition device.

11. A method for physiological and psychological quantification of stress levels of a human subject comprising the following:
   a. acquiring physiological data and psychological data from the human subject by means of a measuring instrument of a data acquisition device;
   b. sending the acquired physiological data and psychological data to a computing platform via a communication link, the physiological data is cardiac signals, motion signals, pulmonary signals, thermal signals, electrodermal activity signals, or brain signals and the psychological data is user feedback, subjective feedback, or environmental feedback;
   c. receiving the acquired physiological data and psychological data from the data acquisition device; and
   d. processing the acquired physiological and psychological data into quantifiable stress metrics by means of a stress function algorithm module to calculate an estimate of levels of hormones or neurotransmitters released by the human subject and therefore the level of stress experienced by the human subject.

12. The method of claim 11, wherein the measuring instrument is an implant device, an ingestible device, a nanotechnology device, a chest strap, a chest patch, a head band, an upper arm band, an upper arm patch, a wrist band, a finger band, a finger patch, an arm sleeve, or a leg sleeve.

13. The method of claim 11, wherein the algorithm is a K-means clustering analysis, a fuzzy clustering, a Gaussian mixture model, a stress rotation model, and an ensemble of the K-means cluster analysis, the fuzzy clustering, the Gaussian mixture model, or the stress rotation model.

14. The method of claim 11, wherein the processing step uses the biological metrics to estimate hormones and/or neurotransmitters released by the human subject during activation of a SAM stress axis.

15. The method of claim 11, wherein the processing step uses the biological metrics to estimate hormones and/or neurotransmitters released by the human subject during activation of the HPA stress axis.

16. The method of claim 11, wherein the stress level experienced by the human subject is average stress levels, levels of acute stress, levels of chronic stress, stress intensity, duration of stressor, levels of distress, or levels of eustress.

17. The method of claim 11, wherein the level of stress is communicated to a third-party database by means of the communication link.

* * * * *